(12) United States Patent
Hwang et al.

(10) Patent No.: US 10,617,817 B2
(45) Date of Patent: Apr. 14, 2020

(54) INFUSION SET ADHESIVE SYSTEMS

(71) Applicant: Becton, Dickinson and Company, Franklin Lakes, NJ (US)

(72) Inventors: Charles Hwang, Wellesley, MA (US); Zhixiong Liu, Bedford, MA (US); Weiyan Nie, Winchester, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 125 days.

(21) Appl. No.: 15/106,231

(22) PCT Filed: Dec. 19, 2014

(86) PCT No.: PCT/US2014/071363
§ 371 (c)(1),
(2) Date: Jun. 17, 2016

(87) PCT Pub. No.: WO2015/095639
PCT Pub. Date: Jun. 25, 2015

(65) Prior Publication Data
US 2016/0310665 A1 Oct. 27, 2016

Related U.S. Application Data

(60) Provisional application No. 61/918,995, filed on Dec. 20, 2013.

(51) Int. Cl.
*A61M 5/158* (2006.01)
*C09J 7/21* (2018.01)
(Continued)

(52) U.S. Cl.
CPC .............. *A61M 5/158* (2013.01); *A61K 8/26* (2013.01); *A61K 8/28* (2013.01); *A61L 29/16* (2013.01);
(Continued)

(58) Field of Classification Search
CPC .......... A61M 25/02; A61M 2005/1586; A61M 2025/0266; A61M 2025/0273; A61M 2025/028
See application file for complete search history.

(56) References Cited

U.S. PATENT DOCUMENTS 4,586,927 A * 5/1986 Jensen .................... A61F 5/442
604/334
5,160,315 A * 11/1992 Heinecke .............. A61F 13/023
206/441
(Continued)

FOREIGN PATENT DOCUMENTS

EP 0507459 A1 10/1992
JP 63-242270 A 10/1988
(Continued)

*Primary Examiner* — Emily L Schmidt
(74) *Attorney, Agent, or Firm* — Dickinson Wright PLLC

(57) ABSTRACT

Improvements in an adhesive patch for an infusion set include the addition of an antiperspirant, wound healing and/or antimicrobial agent to the adhesive surface, and the layering of different backing materials to improve performance characteristics of the patch. Patches may be offered as part of a product line, in which differently shaped patches are provided for attachment to different parts of the body, and different pressure sensitive adhesives provide different peel strength according to different use patterns of the end user.

17 Claims, 3 Drawing Sheets

(51) Int. Cl.
  *C09J 7/38* (2018.01)
  *A61K 8/26* (2006.01)
  *A61K 8/28* (2006.01)
  *A61L 29/16* (2006.01)
  *A61Q 15/00* (2006.01)
  *A61M 5/142* (2006.01)

(52) U.S. Cl.
  CPC ............ *A61Q 15/00* (2013.01); *C09J 7/21* (2018.01); *C09J 7/38* (2018.01); *A61L 2300/404* (2013.01); *A61L 2300/412* (2013.01); *A61M 5/14248* (2013.01); *A61M 2005/14264* (2013.01); *A61M 2005/1586* (2013.01); *A61M 2005/1587* (2013.01); *A61M 2207/00* (2013.01); *C09J 2201/606* (2013.01); *C09J 2205/10* (2013.01); *C09J 2205/102* (2013.01); *C09J 2475/006* (2013.01)

(56) References Cited

U.S. PATENT DOCUMENTS

| | | | | |
|---|---|---|---|---|
| 5,686,096 | A * | 11/1997 | Khan | A61M 25/02 424/443 |
| 6,124,521 | A * | 9/2000 | Roberts | A61M 25/02 602/42 |
| 6,325,565 | B1 | 12/2001 | Girardot et al. | |
| 7,005,556 | B1 * | 2/2006 | Becker | A61L 15/46 424/447 |
| 7,294,752 | B1 * | 11/2007 | Propp | A61M 25/02 602/42 |
| 7,806,873 | B2 | 10/2010 | Dikeman et al. | |
| 7,883,488 | B2 | 2/2011 | Shantha et al. | |
| 2001/0025159 | A1 * | 9/2001 | Fleischer | A61M 25/02 604/174 |
| 2002/0161332 | A1 * | 10/2002 | Ramey | A61M 5/158 604/164.07 |
| 2003/0125668 | A1 * | 7/2003 | Bierman | A61M 25/02 604/174 |
| 2005/0107743 | A1 | 5/2005 | Fangrow, Jr. | |
| 2007/0055205 | A1 * | 3/2007 | Wright | A61F 13/023 604/174 |
| 2007/0123828 | A1 * | 5/2007 | Propp | A61M 25/02 604/180 |
| 2007/0282271 | A1 * | 12/2007 | Kaplan | A61F 5/445 604/174 |
| 2010/0174250 | A1 * | 7/2010 | Hu | A61F 5/4401 604/319 |
| 2010/0331785 | A1 * | 12/2010 | Fabo | A61M 16/047 604/180 |
| 2011/0098622 | A1 * | 4/2011 | Hatanaka | A61F 13/0269 602/52 |
| 2014/0257242 | A1 * | 9/2014 | Sung | A61M 25/02 604/508 |

FOREIGN PATENT DOCUMENTS

| | | | |
|---|---|---|---|
| JP | 2007-111537 A | 5/2007 | |
| JP | 2008-302237 A | 12/2008 | |
| WO | WO-9504511 A1 | 2/1995 | |
| WO | WO-02083206 A2 | 10/2002 | |
| WO | WO-2007113597 A2 | 10/2007 | |
| WO | WO 2014039891 | * 3/2014 | ............ A61M 25/01 |

* cited by examiner

INFUSION SET ADHESIVE SYSTEMS

CROSS REFERENCE TO RELATED APPLICATION

This application claims the benefit of U.S. Provisional Application 61/918,995, filed Dec. 20, 2013, which is incorporated by reference.

BACKGROUND OF THE INVENTION

Field of the Invention

The invention is directed to infusion set adhesive systems for attachment of an infusion set to a wearer's body using a patch.

Description of the Related Art

An infusion set is a device attached to a wearer's body to deliver a medication from an infusion pump to a subcutaneous site on the wearer's body. The infusion set generally comprises a hub, or base, bearing an infusion cannula inserted into the infusion site on the wearer's body, and a tube connecting the cannula to the infusion pump. The hub is attached to a patch which is attached to the wearer's body with an adhesive system such that the infusion set can be removed and replaced every several days.

Many variations on the adhesive patch are practiced in the art, but in general, the adhesive patch comprises a backing layer having a central area receiving the hub and cannula, a layer of adhesive adjacent the backing layer which faces the wearer, and a release liner over the adhesive to prevent the adhesive from becoming contaminated before use. Adhesives for this purpose are typically provided commercially already applied to a backing layer, with a release liner covering the adhesive to prevent the adhesive from being contaminated prior to use.

One conventional backing layer material for the adhesive is nonwoven polyester. The nonwoven provides good structural integrity, but poor water resistance. Also, the nonwoven material has a tendency to curl back at the edges and peel off. Polyurethane sheet, on the other hand, another conventional backing layer material, has good water resistance and conforming characteristics for adhesion, but it can be too flexible, making it difficult for the user to handle without the material folding over and sticking to itself. Thus, another object of the invention is to maximize the performance characteristics of backing layer materials for an infusion set patch.

The adhesive systems known in the art are sensitive to body perspiration which wets and degrades the pressure sensitive adhesive. It is another object of the invention to address the problem whereby body perspiration degrades the performance of the infusion set adhesive system.

The patches sold with infusion sets according to the prior art are typically circular, and in general have not been optimized for attachment to different parts of the body. Thus, a further object of the invention is to provide a product line from which the user can select an adhesive system based on the adhesion site on the body and activity.

The infusion sets known in the prior art are sold with only one choice of peel strength. The inventors herein have recognized that the use of infusion sets has become more nuanced, such that it would be a desirable advance in the art to provide infusion set patches optimized for different end use patterns. Thus, different users could select infusion sets from a product line offering patches with different adhesion strength for different use patterns.

SUMMARY OF THE INVENTION

These and other objects of the invention are achieved according to the invention, in one aspect, with an adhesive system for an infusion set, comprising: a hub having a cannula delivering medication to a subcutaneous site of a user, and tubing directing medication from an infusion pump to the hub; a nonwoven backing layer having a central aperture receiving the hub; a polyurethane backing layer larger than the nonwoven backing layer superposed on the nonwoven backing layer and forming an adhesive surface together with the nonwoven backing layer; a layer of pressure sensitive adhesive over the adhesive surface formed by the nonwoven and polyurethane backing layers facing the user; and a bottom release liner covering the pressure sensitive adhesive layer and having a central aperture. In this way, the backing layer obtains the performance benefits of the structurally reliable nonwoven layer and the water resistance of a polyurethane layer.

To assemble the adhesive system described above, having multiple backing layers, a polyurethane or other backing layer with adhesive pre-applied thereon is applied over the nonwoven or other backing layer which likewise has adhesive pre-applied thereon, so that the layers are secured with adhesive between them and together form the adhesive surface facing the user.

In another aspect, the invention resides in an infusion set adhesive system, comprising: a hub having a cannula for delivering medication to a subcutaneous site of a user, and tubing for directing medication from an infusion pump to the hub; a backing layer having a central aperture receiving the hub; an adhesive layer adjacent the backing layer facing the user; and a removable liner adjacent the adhesive layer; wherein the pressure sensitive adhesive comprises an antiperspirant. The antiperspirant ensures that performance of the pressure sensitive adhesive in the adhesive layer is not degraded over time by the user's body perspiration.

In other aspects, the invention relates to providing a variety of infusion sets according to the preference of the end user. For example, the invention may be embodied as a product line in which at least first and second infusion sets are provided, the first and second infusion set each having a different pressure sensitive adhesive composition to afford a different peel strength. In this way, infusion sets may be provided according to the preference of the end user, so that an elderly patient for example is provided with a soft and flexible patch with relatively weak adhesion, while a more active patient is provided with a patch having greater peel strength.

Similarly, the invention may be embodied as a product line having at least first and second infusion sets, the first and second infusion set each having a different body conformable adhesive patch. In this way, different infusion sets are provided to the end user depending upon how the user chooses to wear the patch.

DETAILED DESCRIPTION OF THE INVENTION

As used herein, an "infusion set" comprises tubing, a cannula-bearing hub, and an adhesive patch for attachment to the user's body. The infusion set is adapted for attachment to an infusion pump, but the pump is not part of the set as that term is used in the present disclosure.

Figure 1:
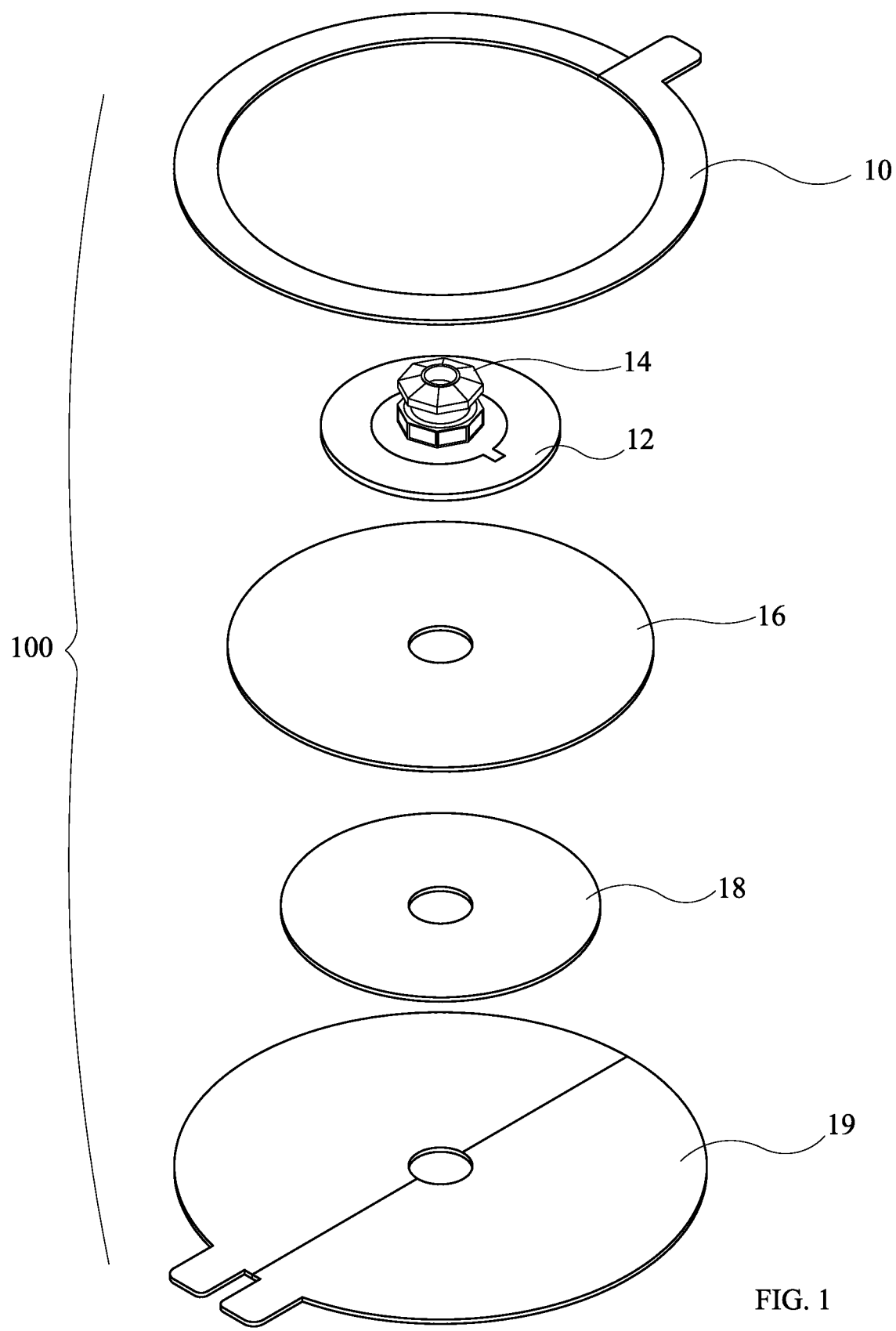
FIG. 1 is an exploded view of an infusion set according to the invention, without the tubing or cannula.
Figure 2:
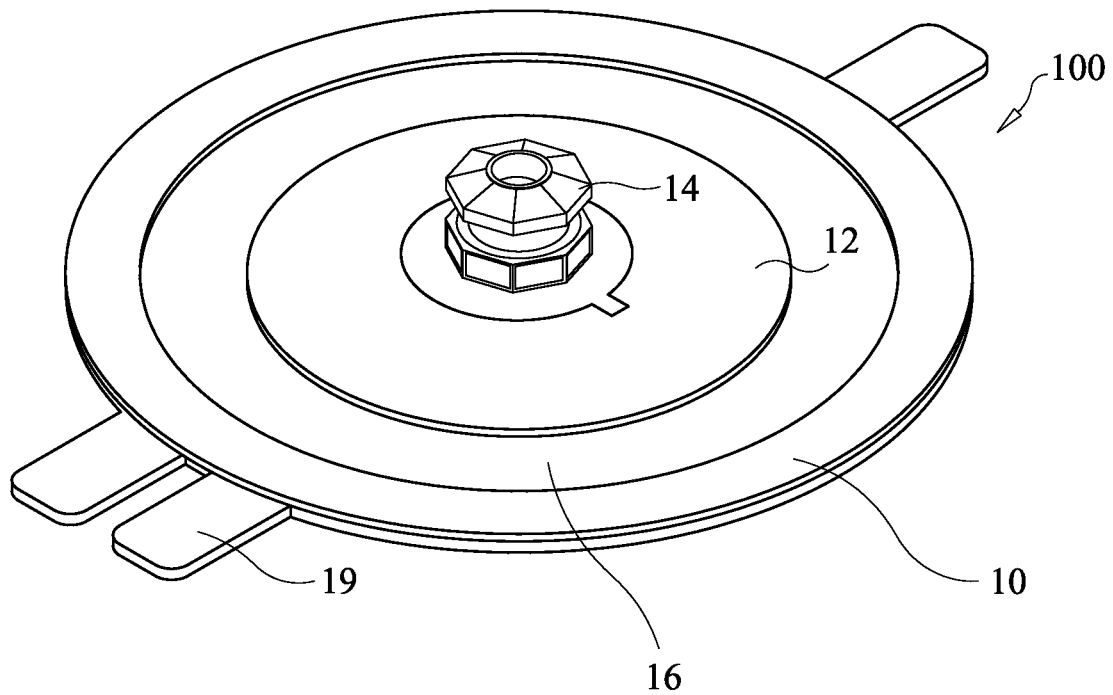
FIG. 2 is an assembled view of the infusion set of FIG. 1.

According to one embodiment depicted in FIG. 1, the infusion set 100 comprises bottom liner 19, nonwoven backing layer 18, and polymeric backing layer 16. Both the nonwoven backing layer 18 and the polymeric backing layer 16 support a pressure sensitive adhesive facing the user's body for attachment of the infusion set to the infusion site. The polyurethane backing layer 16 is larger than the nonwoven layer so that the two backing layers together form an adhesive surface. A portion of the pressure sensitive adhesive is on the perimeter of the adhesive surface, adjacent the polyurethane layer, and another portion is toward the center of the patch, adjacent the nonwoven layer. In general, adhesives are provided with a backing layer in place, so that the adhesive system is assembled by superposing one backing layer over the other so that the two layers are secured together forming an adhesive surface on the opposite side.

In embodiments, the pressure sensitive adhesive layer covers substantially the entire extent of the adhesive surface. Alternatively, regions of the adhesive surface are covered with a pressure sensitive adhesive and adjacent regions are covered with active agents such as an antiperspirant or wound healing agent. This configuration would be preferable if the active agent is expected to degrade the performance of the pressure sensitive adhesive after prolonged contact. Applying pressure sensitive adhesive in a region distinct from an active agent region also permits the infusion set to be tailored according to the user's skin sensitivity. For example, the area near the injection site may be especially sensitive, and it may be preferable to limit an active agent, such as an antiperspirant, to an area of the adhesive surface out of contact with the injection site. With wound healing or antimicrobial agents it may be desirable to combine the active agent and the pressure sensitive adhesive in one composition. As would be understood by the person of ordinary skill in the art, some minor area of the adhesive surface could be left uncovered by adhesive or active agent(s), provided the functioning of the patch is not deleteriously impacted.

A hub 14 connects directly to the cannula (not shown), which may be inserted into the subcutaneous site on the wearer's body through a central aperture in the backing layers 16, 18 using mechanisms known in the art. Using a central nonwoven layer 18 ensures that the patch is easily applied and maintains structural integrity of the patch, while an outer layer of polyurethane 16 ensures that the patch is water resistant. The nonwoven patch may be polyester or other fiber material known in the art for the like purpose.

Pressure sensitive adhesives ("PSAs") based on polymers having acrylic or acrylate moieties are well known in the art and have been used for many years in the medical devices arts. Other PSAs may be based on silcones. The selection of an appropriate PSA having the desired peel strength may be left to the skill of the person of ordinary skill in this art. Peel strength is a measure of how firmly the PSA adheres to the user's body and may be measured in various ways, measuring the force required to separate two reference surfaces adhered with the PSA. In some embodiments, the PSA is modified by adding one or more active agents, such as an antimicrobial, wound-healing or antiperspirant agent directly to the PSA composition.

Antiperspirant active agent(s) known in the art for inclusion in medical or cosmetic applications may be used in the adhesive system according to the invention. Many of the known antiperspirant agents used in this context include, without limitation, aluminum salts and/or zirconium salts, complexes of zirconium hydroxychloride and of aluminum hydroxychloride, for example, aluminum chlorohydrate, aluminum chlorohydrex-propylene glycol complex, aluminum dichlorohydrate, aluminium dichlorohydrex-polyethylene glycol complex, aluminum dichlorohydrex-propylene glycol complex, aluminum sesquichlorohydrate, aluminum sesquichlorohydrex-polyethylene glycol complex, and aluminum sesquichlorohydrex-propylene glycol complex, etc. These agents may be provided in a solvent and combined with the PSA in an amount that does not deleteriously affect the performance characteristics of the PSA. Alternatively, the antiperspirant may be co-deposited with the PSA on the adhesive surface, in a pattern of concentric rings, alternating PSA and antiperspirant, for example.

Adjacent the PSA on the patient-facing side of the hub, is bottom release liner 19, which covers the PSA and prevents contamination of the patch prior to use. A silicone wax-coated paper or other conventional release material may be used as the bottom backing liner. On the backing layers on the top of the device is a top reinforcing layer 10, which covers the edge of the polyurethane backing layer (in the particular embodiment shown). The reinforcing layer is provided to provide a temporary support for the edges of the polyurethane layer that are not supported by the nonwoven backing layer 18. The polyurethane layer is so flexible that the patch may be compromised before use if it is unsupported by a reinforcing layer.

Tabs are provided on both the bottom release liner and the top reinforcing layer, oriented on opposite sides of the patch. The tabs are adapted to be grasped by the user to remove the liner. The bottom liner 19 can be scored so that it is removed in pieces, while the top reinforcing layer 10 has a tab configured to remove the ring-shaped reinforcement in a single piece.

The dimensions of the adhesive patch are not critical and may be adapted according to conventional configurations practiced in the art. Generally the release liner is a thin planar element, having a thickness in the neighborhood of 0.01 inches, although the exact thickness is not critical. The patches may be sized as known in the art, with a typical diameter of the patch at the widest point being 1.5 to 2.5 inches, although this dimension likewise is not critical. The central aperture of all the layers may be a circle having a diameter of 0.25 to 0.35 inches, depending on the requirements of receiving the hub.

Figure 3:
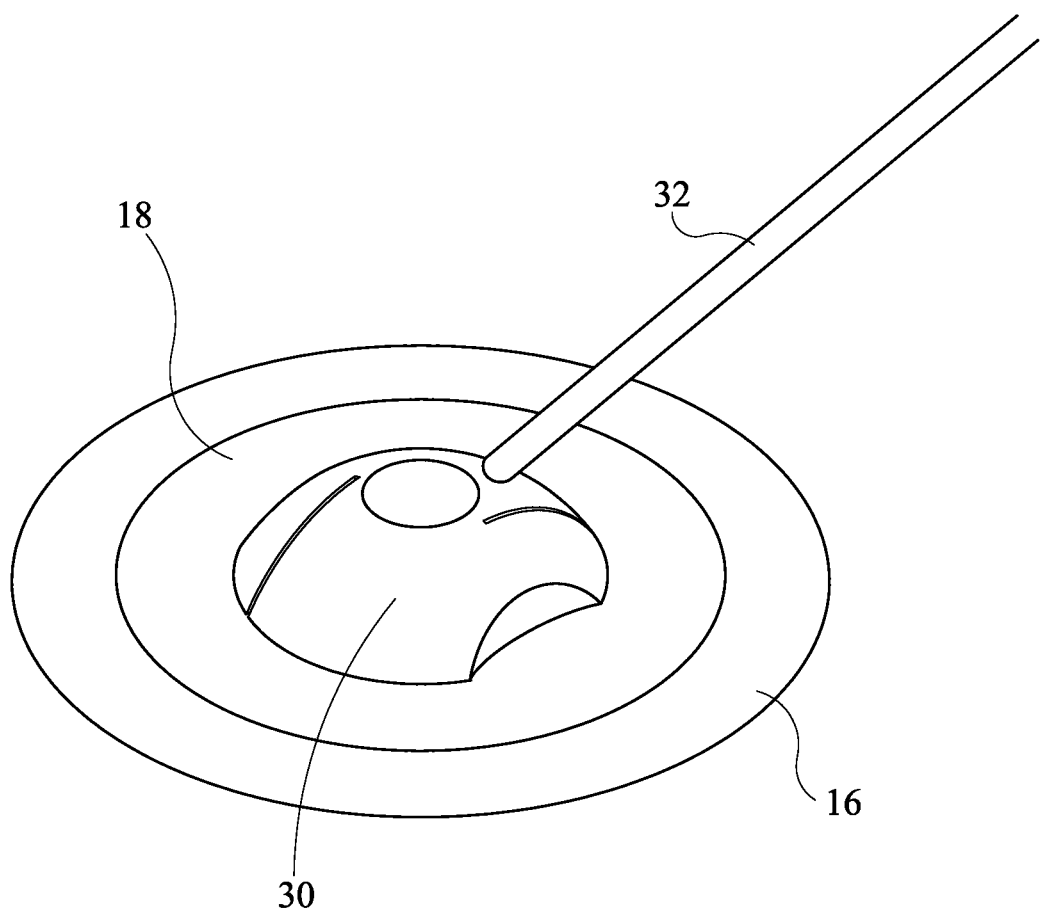
FIG. 3 is a perspective view of an assembled infusion set from the top side.

Hub 14 may be made of a relatively rigid plastic, such as (without limitation) acrylonitrile butadiene styrene (ABS) which can be co-molded in a two-shot process with a more flexible elastomeric base material 12 to make an integral structure. FIG. 3 depicts the top of the device, with an outer housing 30 added over the hub and tubing 32 to direct medication from the infusion pump.

A "product line," as used herein, consists of a plurality of infusion sets usable with the same infusion pump. The infusion sets in a product line have similar appearance, some identical parts, and may be branded as a family of infusion sets, but each infusion set in a product line differs in a particular feature, such as the peel strength of the adhesive, and/or the shape of the patch, so that the infusion set can be used in accordance with a particular need or preference of a user. In one embodiment, a product line includes a variety of infusion sets each having a different patch shape. To conform to a portion of the body that experiences significant twisting, for example, the patch may be provided with lateral extension, approximating an overall "H" shape. Crescent or other shapes may also be adapted for particular infusion sites. The non-woven layer may be provided with slits so that the material can stretch.

A product line may also be offered with different adhesion strengths, so that an active user is provided with an extra strong adhesive, a normal user is provided with a typical strength adhesive, as currently practiced, and an elderly or frail patient, or patient with particularly sensitive skin, may be provided with a weaker adhesion strength adhesive. In this way, users may be able to select adhesive strength as users currently select catheter length and extension tubing length, depending on a particular use pattern.

The foregoing description of the preferred embodiments is not to be deemed limiting of the invention, which is defined by the appended claims. The person of ordinary skill in the art, relying on the foregoing disclosure, may practice variants of the embodiments described without departing from the scope of the invention claimed. A feature or dependent claim limitation described in connection with one embodiment or independent claim may be adapted for use with another embodiment or independent claim, without departing from the scope of the invention.

What is claimed is:

1. An adhesive system for an infusion set, comprising:
   a hub having a cannula adapted for delivering medication to a subcutaneous site of a user;
   tubing adapted for directing medication from an infusion pump to the hub;
   a nonwoven backing layer having a central aperture receiving the hub;
   a backing layer larger than the nonwoven backing layer superposed on the nonwoven backing layer and forming a user surface together with the nonwoven backing layer;
   a layer of pressure sensitive adhesive over a region of the user surface facing the user; and
   a top reinforcing layer on a side facing away from the user, the top reinforcing layer having a central aperture and a diameter larger than a diameter of the backing layer;
   wherein:
      the backing layer has a central aperture, each of the backing layer and nonwoven backing layer central apertures receives the cannula, and the hub surrounds the central aperture of the backing layer;
      the adhesive system further comprises an active agent on the user surface; and
      the region of the user surface is covered with the pressure sensitive adhesive and an adjacent region of the user surface is covered with the active agent and not covered with any adhesive.

2. The adhesive system according to claim 1, wherein the nonwoven backing layer comprises nonwoven polyester.

3. The adhesive system according to claim 1, further comprising a bottom release liner covering the pressure sensitive adhesive layer and having a central aperture;
   wherein the bottom release liner is scored for removal in pieces and comprises a bottom tab extending from the periphery of the backing layer.

4. The adhesive system according to claim 3, wherein the top reinforcing layer comprises at least one top tab extending from the periphery of the backing layer, in a direction opposite the bottom tab on the bottom release liner.

5. The adhesive system according to claim 1, wherein the active agent comprises a wound-healing agent.

6. The adhesive system according to claim 1, wherein the active agent is limited to an area of the user surface out of contact with an injection site of the cannula.

7. The adhesive system according to claim 1, wherein the backing layer comprises a polymeric backing layer.

8. A product line of infusion sets with adhesive systems according to claim 1, comprising:
   at least first and second infusion sets, the first and second infusion sets each having a different body-conformable adhesive patch.

9. The product line according to claim 8, wherein the first and second sets differ in the shape of the body conformable adhesive patch.

10. A product line of infusion sets with adhesive systems according to claim 1, comprising:
    at least first and second infusion sets, the first and second infusion sets each having a different pressure sensitive adhesive composition to afford a different peel strength.

11. The product line according to claim 10, wherein the first and second infusion sets differ only in the peel strength of the pressure sensitive adhesive.

12. The product line according to claim 11, comprising at least first, second and third infusion sets, each having a different level of peel strength.

13. An adhesive system for an infusion set, comprising:
    a hub having a cannula adapted for delivering medication to a subcutaneous site of a user;
    tubing adapted for directing medication from an infusion pump to the hub;
    a nonwoven backing layer having a central aperture receiving the hub;
    a backing layer larger than the nonwoven backing layer superposed on the nonwoven backing layer and forming a user surface together with the nonwoven backing layer; and
    a layer of pressure sensitive adhesive over a region of the user surface facing the user;
    wherein the backing layer has a central aperture, each of the backing layer and nonwoven backing layer central apertures receive the cannula, and the hub closes surrounds the central aperture of the backing layer.

14. The adhesive system according to claim 13, further comprising a top reinforcing layer on a side facing away from the user, the top reinforcing layer having a central aperture and a diameter larger than a diameter of the backing layer.

15. An adhesive system for an infusion set, comprising:
    a hub having a cannula adapted for delivering medication to a subcutaneous site of a user;
    tubing adapted for directing medication from an infusion pump to the hub;
    a nonwoven backing layer having a central aperture receiving the hub;
    a backing layer larger than the nonwoven backing layer superposed on the nonwoven backing layer and forming a user surface together with the nonwoven backing layer;
    a layer of pressure sensitive adhesive over a portion of the user surface facing the user; and
    a removable top reinforcing layer on a side facing away from the user, the top reinforcing layer having a central aperture;
    wherein:

the backing layer has a central aperture, and each of the backing layer and nonwoven backing layer central apertures receives the cannula;

the adhesive system further comprises an active agent on the user surface; and a majority of the hub is disposed more proximally than the proximal most layer of the adhesive system.

16. The adhesive system according to claim 15, wherein the active agent is limited to an area of the user surface out of contact with an injection site of the cannula.

17. The adhesive system according to claim 15, wherein the hub covers the backing layer and nonwoven backing layer central apertures.

* * * * *